(12) United States Patent
Yao et al.

(10) Patent No.: US 6,808,908 B2
(45) Date of Patent: Oct. 26, 2004

(54) FUNCTIONALIZED POROUS SUBSTRATE FOR BINDING CHEMICAL AND BIOLOGICAL MOIETIES

(75) Inventors: Li Yao, Peachtree City, GA (US); George Warren Greene, IV, Peachtree City, GA (US); Guoqiang Mao, Smyrna, GA (US); Xingguo Li, Peachtree City, GA (US)

(73) Assignee: Porex Technologies Corporation, College Park, GA (US)

( * ) Notice: Subject to any disclaimer, the term of this patent is extended or adjusted under 35 U.S.C. 154(b) by 27 days.

(21) Appl. No.: 09/866,842

(22) Filed: May 30, 2001

(65) Prior Publication Data

US 2003/0100086 A1 May 29, 2003

(51) Int. Cl.[7] .......................... C12N 11/06; C12N 11/14; G01N 33/549; C07K 17/06; C07K 17/08
(52) U.S. Cl. .................. 435/181; 424/486; 435/176; 435/180; 436/524; 436/531; 436/532; 530/402; 530/811; 530/815; 530/816
(58) Field of Search .................. 435/176, 177, 435/180, 181, 182; 530/402, 811, 815, 816; 424/486; 436/524, 531, 532

(56) References Cited

U.S. PATENT DOCUMENTS

| | | | | | |
|---|---|---|---|---|---|
| 4,384,045 | A | * | 5/1983 | Ho et al. .................. | 435/176 |
| 4,855,234 | A | * | 8/1989 | Hendrickson et al. ...... | 435/181 |
| 4,897,468 | A | * | 1/1990 | Oka et al. .................. | 530/811 |
| 5,552,325 | A | * | 9/1996 | Nochumson et al. ....... | 436/177 |
| 5,773,308 | A | * | 6/1998 | Conrad et al. ............. | 436/527 |
| 6,004,786 | A | * | 12/1999 | Yamashita et al. .......... | 435/176 |
| 6,524,489 | B1 | * | 2/2003 | Palm et al. ................. | 210/777 |

* cited by examiner

*Primary Examiner*—David M. Naff
(74) *Attorney, Agent, or Firm*—Jones Day

(57) ABSTRACT

The invention relates to porous polymeric materials, methods of making them, and applications in medical devices. A specific embodiment of the invention encompasses a material comprising a porous polyolefin substrate containing inclusions of a material to which chemical or biological moieties are attached directly or via a spacer.

25 Claims, 6 Drawing Sheets

FUNCTIONALIZED POROUS SUBSTRATE FOR BINDING CHEMICAL AND BIOLOGICAL MOIETIES

1. FIELD OF THE INVENTION

Figure 1:
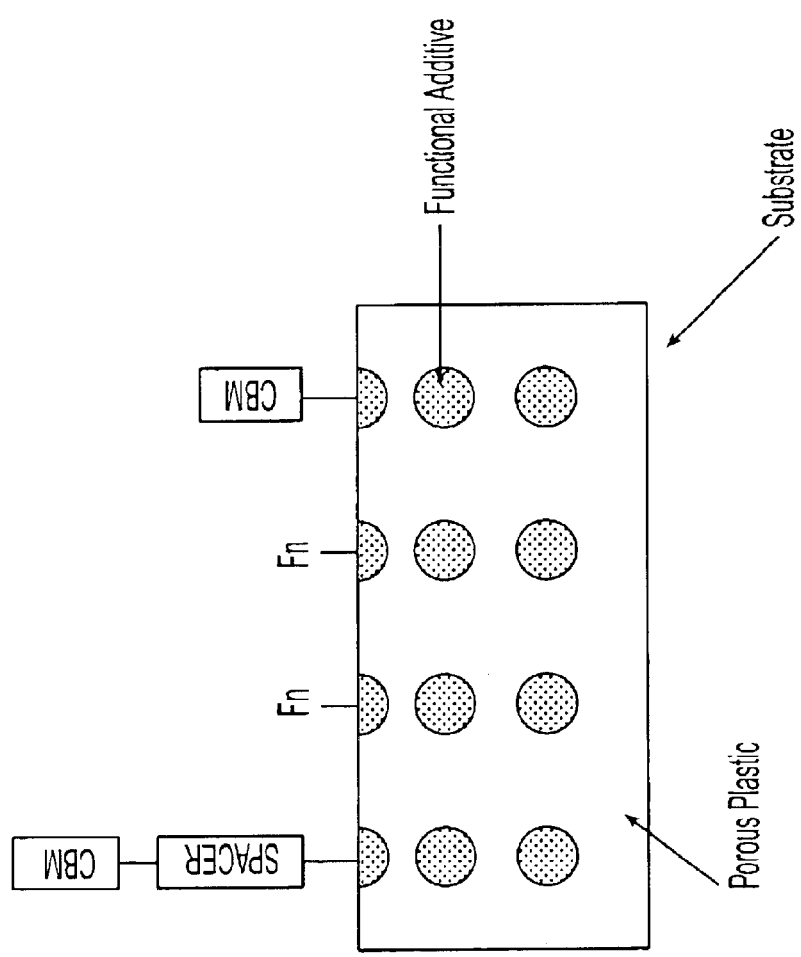

The invention relates to porous polymeric materials to which chemical or biological moieties have been attached, and methods for making the same.

2. BACKGROUND OF THE INVENTION

Porous polymeric materials can be used in a variety of applications. Their uses include medical devices that serve as substitute blood vessels, synthetic and intraocular lenses, electrodes, catheters, and extracorporeal devices such as those that are connected to the body to assist in surgery or dialysis. Porous polymeric materials can also be used as filters for the separation of blood into component blood cells and plasma, microfilters for removal of microorganisms from blood, and coatings for opthalmic lenses to prevent endothelial damage upon implantation.

Bonding materials other than polymers to porous polymeric materials can alter the properties of porous polymers. A combination of properties may provide porous polymers suitable for the above mentioned purposes. This combination, however, has been difficult to achieve because of the natural properties of polymers.

The hydrophobic nature of typical polymers, however, has limited the usefulness of porous materials made from them. For example, proteins will often denature when placed in contact with such materials. But contact lenses, implants, and related devices that are in intimate contact with the body must have hydrophilic surfaces that are biologically compatible.

The physical and/or chemical properties of a plastic surface can be changed by adhering or bonding a different material to it. Examples of this technique are disclosed by U.S. Pat. No. 4,619,897, which is directed to a porous resin membrane, and by U.S. Pat. No. 4,973,493, which is directed to a device with a biocompatible surface. Other examples of surface modification are provided by U.S. Pat. Nos. 5,077,215, 5,183,545, and 5,203,997, which disclose the adsorption of anionic and nonionic fluorocarbon surfactants onto the surface of fluorocarbon support members.

Further examples of surface modification can be found in U.S. Pat. No. 5,263,992, which discloses the adsorption of polymeric chains onto a support member, and in U.S. Pat. No. 5,308,641, which discloses the covalent attachment of a polyalkylimine to an aminated substrate.

Despite the different techniques available for modifying the surface of polymeric materials, most are limited in their ability to control the degree to which a surface is modified, and many are expensive, inefficient, or cannot be use to modify porous surfaces without coating or clogging their pores. A need exists for polymeric materials that can alter their functionality depending upon incorporation of additives and/or post treatment of these additives. The present invention provides new porous polymeric materials and methods of their manufacture that address this need.

3. SUMMARY OF THE INVENTION

This invention encompasses novel porous materials and methods of their manufacture. Materials of the invention comprise a porous substrate to which chemical or biological moieties are bound directly or by a spacer.

A first embodiment of the invention encompasses a material comprising: a porous substrate comprised of a polymer and a functional additive and having a surface, wherein the surface comprises a region defined by at least some of the functional additive; and a biological or chemical moiety covalently or non-covalently bound to the region. In a preferred material encompassed by this embodiment, the surface comprises a plurality of regions defined by at least some of the functional additive, each of which is covalently bound to a chemical or biological moiety.

A second embodiment of the invention encompasses a material comprising: a porous substrate comprised of a polymer and a functional additive and having a surface, wherein the surface comprises a region defined by at least some of the functional additive; a spacer covalently or non-covalently bound to the region; and a biological or chemical moiety covalently or non-covalently bound to the spacer. In a preferred material encompassed by this embodiment, the surface comprises a plurality of regions defined by at least some of the functional additive, each of which is covalently bound a spacer, which in turn is bound to a biological moiety.

Examples of polymers from which materials of the invention can be made include, but are not limited to, polyolefins, polyethers, nylons, polycarbonates, poly(ether sulfones), or mixtures thereof. Polyethers include, but are not limited to, polyether ether ketone (PEEK, poly(oxy-1,4-phenylene-oxy-1,4-phenylene-carbonyl-1,4-phenylene)), polyether sulfone (PES), or mixtures thereof. Polyolefins include, but are not limited to, ethylene vinyl acetate; ethylene methyl acrylate; polyethylenes; polypropylenes; ethylene-propylene rubbers; ethylene-propylene-diene rubbers; poly(l-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly (vinylidene chloride); poly(tetrafluoroethylene) (PTFE); poly(vinylidene fluoride) (PVDF); acrylonitrile-butadiene-styrene (ABS); or mixtures thereof. Preferred polyolefins are polyethylene or polypropylene.

Functional additives are materials that contain functional groups such as, but not limited to, hydroxyl, carboxylic acid, anhydride, acyl halide, alkyl halide, aldehyde, alkene, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide. Preferred functional groups are hydroxyl, amine, aldehyde, or carboxylic acid. A particularly preferred functional group is hydroxyl. Examples of functional additives include, but are not limited to, silica powder, silica gel, chopped glass fiber, controlled porous glass (CPG), glass beads, ground glass fiber, glass bubbles, kaolin, alumina oxide, or other inorganic oxides.

Examples of spacers useful in the second embodiment of the invention include, but are not limited to, silanes, functionalized silanes (functional groups such as aldehyde, amino, epoxy, halides, etc.), diamines, alcohols, esters, glycols (such as polyethylene glycol), anhydrides, dialdehydes, terminal difunctionalized polyurethanes, diones, macromer, difunctional and multifunctional polymers with end groups, including, but not limited to, amino, carboxylic acid, ester, aldehyde, or mixtures thereof. In a preferred material, the spacer to which the porous substrate and biological or chemical moiety is attached is of Formula I:

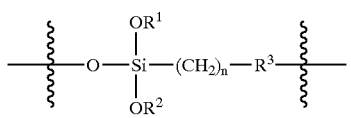

Formula I wherein the bond broken by a wavy line are those between the spacer and the substrate or other moieties; $R^1$ and $R^2$ each independently is hydrogen, substituted or unsubstituted alkyl, aryl, or aralkyl; $R^3$ is a substituted or unsubstituted aliphatic chain or a bond; and n is an integer from about 1 to about 18, preferably, n is an integer from about 1 to about 10, and more preferably from about 2 to about 5.

A variety of chemical and biological moieties can be attached to the porous substrate or spacer of materials of the invention. Examples include, but are not limited to, drugs (e.g., pharmaceuticals), hydrophilic moieties, catalysts, antibiotics, antibodies, antimycotics, carbohydrates, cytokines, enzymes, glycoproteins, lipids, nucleic acids, nucleotides, oligonucleotides, polynucleotides, proteins, peptides, ligand, cells, ribozymes, or combinations thereof.

A specific material of the invention comprises a porous polyethylene substrate having a surface in which a functional additive has been embedded, and a spacer precursor of Formula II covalently attached to at least a portion of said functional additive:

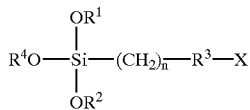

Formula II wherein $R^1$, $R^2$, and $R^4$ each independently is hydrogen, substituted or unsubstituted alkyl, aryl, or aralkyl; $R^3$ is a substituted or unsubstituted aliphatic chain or a bond; X is a group capable of bonding to a biological or chemical moiety, such as OH, $NH_2$, CHO, $CO_2H$, NCO, epoxy, and the like, preferably, X is $NH_2$ or CHO; and n is an integer from about 1 to about 18, preferably, n is an integer from about 1 to about 10, and more preferably from about 2 to about 5.

Still another specific material of the invention comprises a porous polyethylene substrate having a surface in which a functional additive has been embedded, and a spacer of Formula I covalently attached to at least a portion of said functional additive and to a chemical or biological moiety. Preferably, the chemical or biological moiety is a nucleotide, oligonucleotide, polynucleotide, peptide, cell, ligand, or protein.

A third embodiment of the invention encompasses a method of providing a material which comprises: forming a porous substrate comprised of a polymer and a functional additive and having a surface, wherein the surface comprises a region defined by at least some of the functional additive, wherein the region contains at least one functional group; contacting the functional group with a spacer under reaction conditions suitable for the formation of a covalent bond between an atom of the functional group and an atom of the spacer; and contacting the spacer with a chemical or biological moiety under reaction conditions suitable for the formation of a covalent bond or non-covalent bond between an atom of the spacer and an atom of the chemical or biological moiety.

In a preferred method, the functional group is hydroxyl, carboxylic acid, anhydride, acyl halide, alkyl halide, aldehyde, alkene, amide, amine, guanidine, malimide, thiol, sulfonate, sulfonyl halide, sulfonyl ester, carbodiimide, ester, cyano, epoxide, proline, disulfide, imidazole, imide, imine, isocyanate, isothiocyanate, nitro, or azide. Preferred functional groups are hydroxyl, amine, aldehyde, and carboxylic acid.

A fourth embodiment of the invention encompasses a method of providing a material which comprises: forming a porous substrate comprised of a polymer and a functional additive and having a surface, wherein the surface comprises a region defined by at least some of the functional additive, wherein the region contains at least one hydroxyl group; and contacting the hydroxyl group with a compound of Formula II:

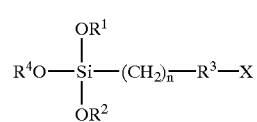

Formula II wherein $R^1$, $R^2$, $R^4$, X, and n are as defined above, under conditions suitable for the formation of a material of Formula III:

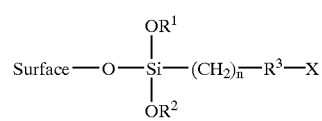

Formula III wherein $R^1$, $R^2$, X, and n are as defined above for Formula II; and Surface is the surface of the substrate.

The porous substrate may be formed by at least two methods. In one method, beads are sintered together with other polymer beads prior to attaching compounds of Formula II or IV. In another method, compounds of Formula II or IV are attached to the surface of beads prior to sintering the beads to form the porous substrate.

In a specific method of this embodiment, the material of Formula III is contacted with a chemical or biological moiety having an amine group if X is an aldehyde or carboxylic acid, or a chemical or biological moiety having an aldehyde or carboxylic acid group if X is an amine, under reaction conditions suitable for the formation of a material of Formula IV:

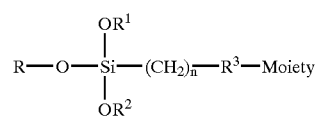

Formula IV wherein $R^1$, $R^2$, $R^3$, and n are defined as above for Formula II; R is the porous substrate surface and Moiety is a chemical or biological moiety.

In another specific method of this embodiment, the material of Formula IV wherein X is $NH_2$ is contacted with a compound of Formula V:

Formula V wherein Spacer is a hydrophilic segment and Z is a terminal group capable of covalently or non-covalently bonding to proteins, amino acids, oligonucleotides, and the like, under reaction conditions suitable for the formation of a material of Formula VI:

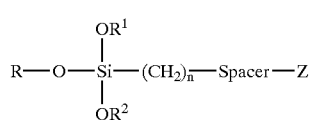

Formula VI wherein R is the surface of the porous substrate; and $R^1$, $R^2$, and n are defined as above for Formula II.

Preferably, the Spacer is a hydrophilic polyurethane, polyethylene glycol, or polyelectrolytes with terminal groups (Z) capable of bonding to proteins, amino acids, oligonucleotides wherein Z includes, but is not limited to, isocyanurate, aldehydes, amines, carboxylic acids, N-hydroxysuccimide, and the like.

A sixth embodiment of the invention encompasses a method of controlling the functionalization of a sintered polyolefin substrate which comprises: forming a mixture of polyolefin particles and particles of a functional additive; and sintering the mixture; wherein the functional additive comprises functional groups and the concentration of functional additive in the mixture is approximately proportional to the density of functional groups on a surface of the sintered polyolefin substrate. In a preferred embodiment, the functional additive is silica powder, silica gel, chopped glass fiber, controlled porous glass (CPG), glass beads, ground glass fiber, glass bubbles, kaolin, alumina oxide, or other inorganic oxides.

3.1. Definitions

As used herein and unless otherwise indicated, the term "alkyl" includes saturated mono- or di-valent hydrocarbon radicals having straight, cyclic or branched moieties, or a combination of the foregoing moieties. An alkyl group can include one or two double or triple bonds. It is understood that cyclic alkyl groups comprise at least three carbon atoms.

As used herein and unless otherwise indicated, the term "aralkyl" includes an aryl substituted with an alkyl group or an alkyl substituted with an aryl group. An example of aralkyl is the moiety —$(CH_2)_p$Ar, wherein p is an integer of from 1 to about 4, 8, or 10.

As used herein and unless otherwise indicated, the term "aryl" includes an organic radical derived from an aromatic hydrocarbon by removal of one hydrogen, such as phenyl or naphthyl.

As used herein and unless otherwise indicated, the term "halo" means fluoro, chloro, bromo, or iodo. Preferred halo groups are fluoro, chloro, or bromo.

As used herein and unless otherwise indicated, the term "non-covalent" when used to describe a bond, means a bond formed by ionic interactions, Van der Waals interactions, hydrogen bonding interactions, steric interactions, hydrophilic interactions, or hydrophobic interactions between two atoms or molecules.

As used herein and unless otherwise indicated, the term "substituted," when used to describe a chemical moiety, means that one or more hydrogen atoms of that moiety are replaced with a substituent. Examples of substituents include, but are not limited to, alkyl and halo.

As used herein and unless otherwise indicated, the term "heteroaryl" means an aryl group wherein at least one carbon atom has been replaced with an O, S, P, Si, or N atom.

As used herein and unless otherwise indicated, the terms "heterocyclic group" and "heterocycle" include aromatic and non-aromatic heterocyclic groups containing one or more heteroatoms each selected from O, S, P, Si, or N. Non-aromatic heterocyclic groups must have at least 3 atoms in their ring system, but aromatic heterocyclic groups (i.e., heteroaryl groups) must have at least 5 atoms in their ring system. Heterocyclic groups include benzo-fused ring systems and ring systems substituted with one or more oxo moieties. An example of a 3 membered heterocyclic group is epoxide, and an example of a 4 membered heterocyclic group is azetidinyl (derived from azetidine). An example of a 5 membered heterocyclic group is thiazolyl, and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such attachment is possible. For instance, a group derived from pyrrole can be pyrrol-1-yl (N-attached) or pyrrol-3-yl (C-attached).

As used herein, unless otherwise indicated, the term "polyelectrolyte" means a polymer having electronic charges. The polyelectrolyte may exist in a complex form, which is also called symplexes. Polyelectrolytes are divided into polyacids, polybases, and polyampholytes. Depending on the charge density in the chain, polyelectrolytes are divided into weak and strong. The charge of weak polyelectrolytes is determined by dissociation constants of ionic groups and pH of the solution. Strong polyelectrolytes in water solutions are mostly ionized independent of the solution's pH. Typical weak polyacid polyelectrolytes include, but are not limited to, poly(acrylic acid) and poly (methacrylic acid). Strong polyacid polyelectrolytes include, but are not limited to, poly(ethylenesulfonic acid), poly (styrenesulfoinic acid), and poly(phosphoric acid). Weak polybase polyelectrolytes include, but are not limited to, poly(4-vinylpyridine), polyethyleneimine (PEI), and polyvinylamine. Strong polybase polyelectrolytes can be obtained by alkylation of nitrogen, sulfur, or phosphorus atoms of weak polybase polyelectrolytes. See "Concise Polymeric Materials Encyclopedia" (Joseph C. Salamone, 1999 by CRC Press LLC, ISBN 0-84932-226-X, pages 1140–1141).

3.2. FIGURES

Figure 2:
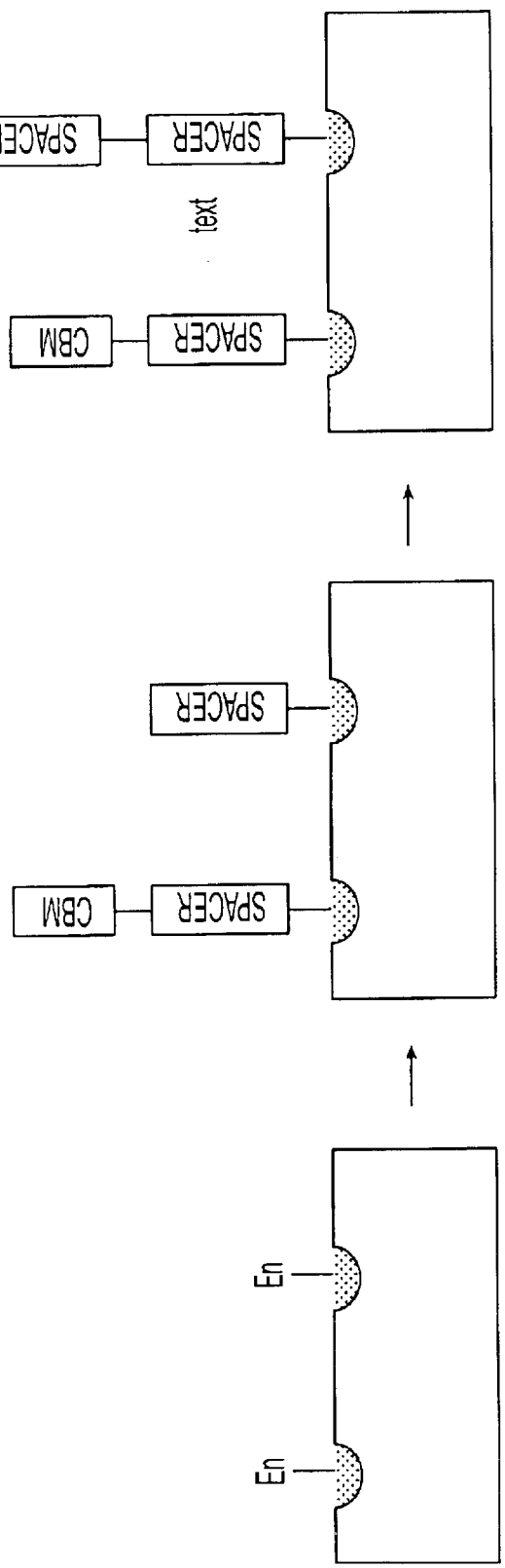
Figure 3:
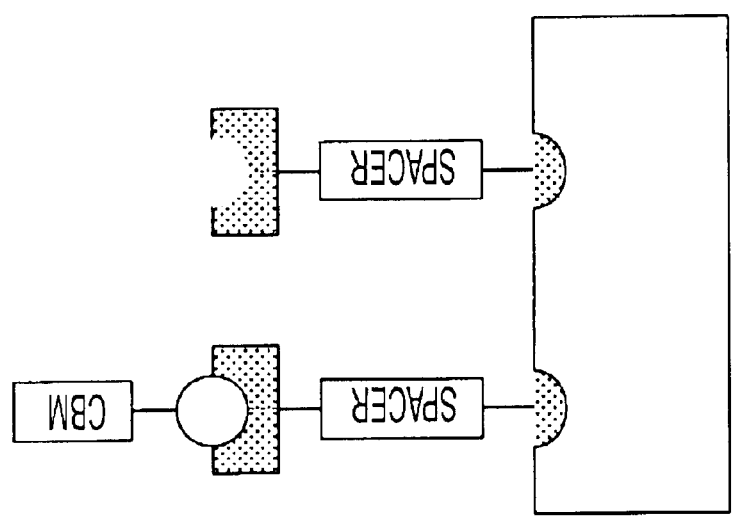
Figure 4:
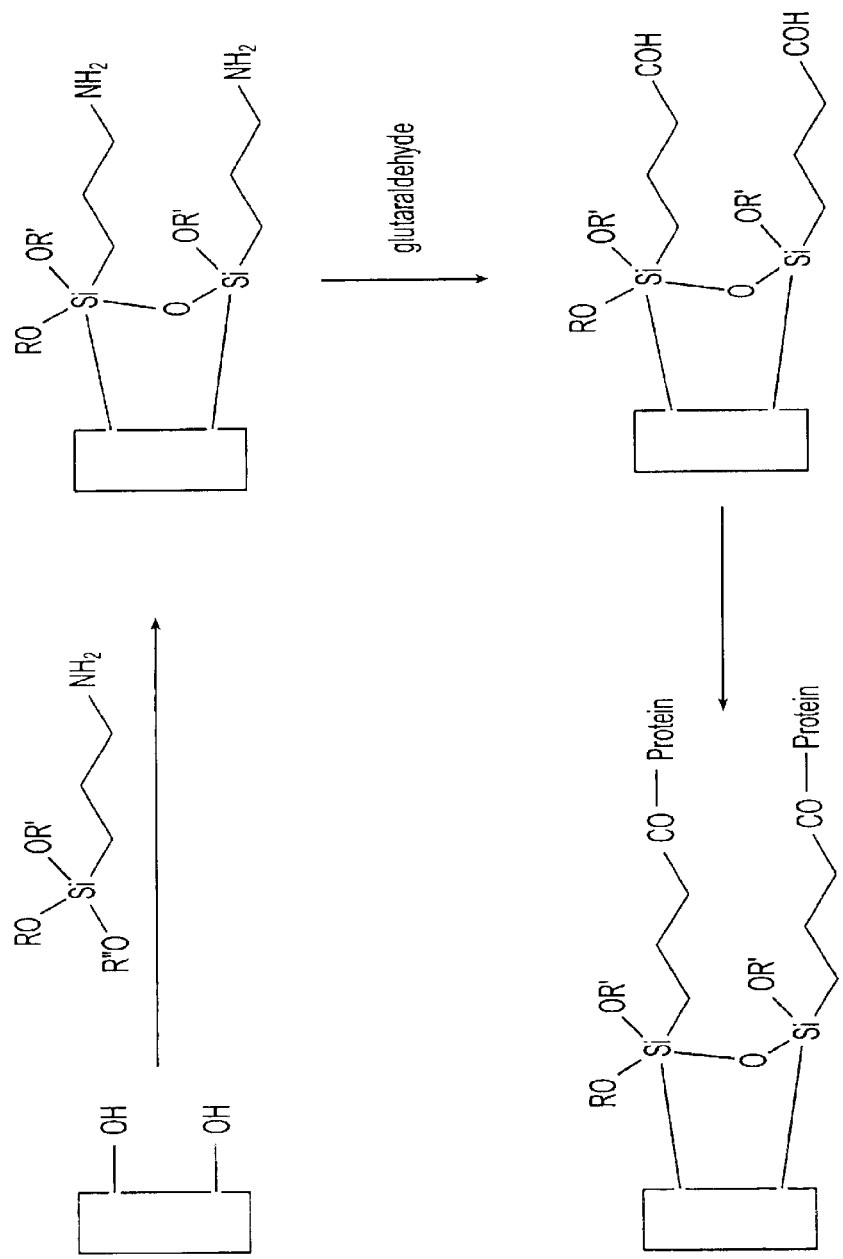
Figure 5:
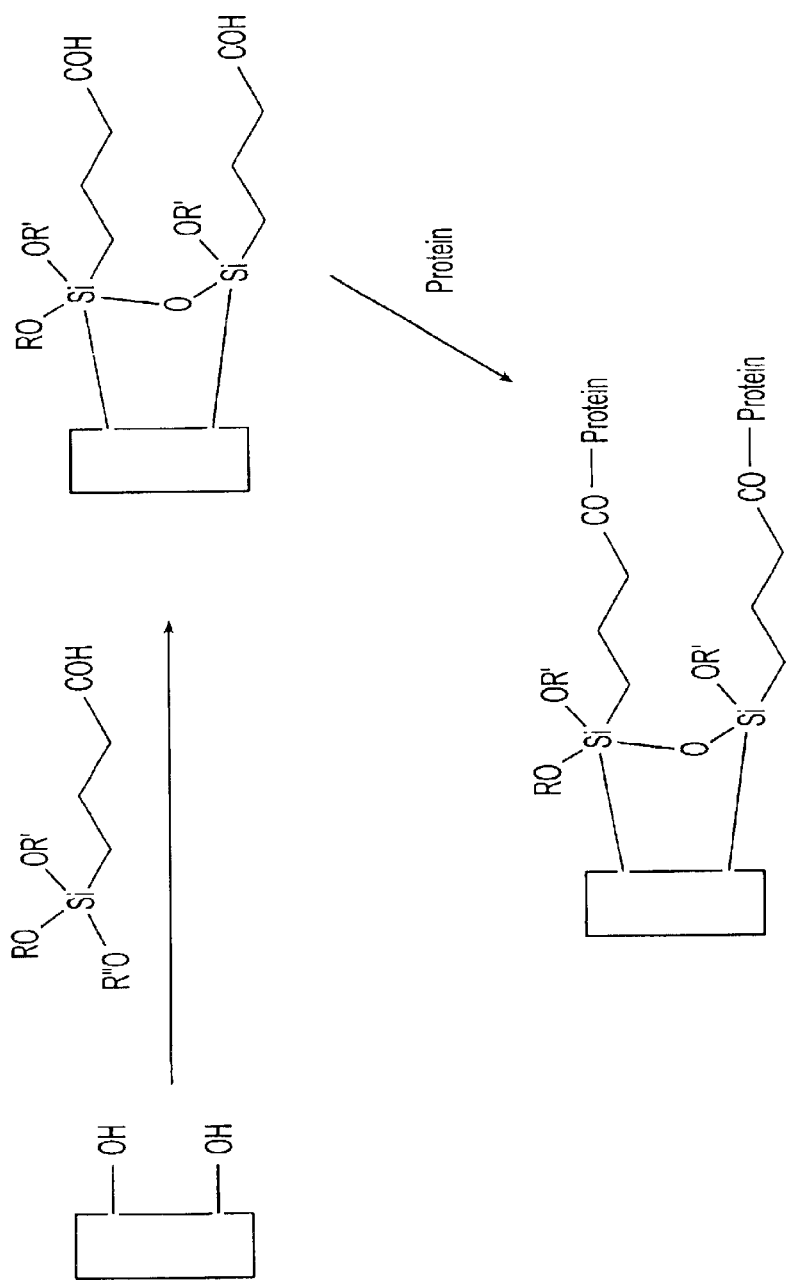
Figure 6:
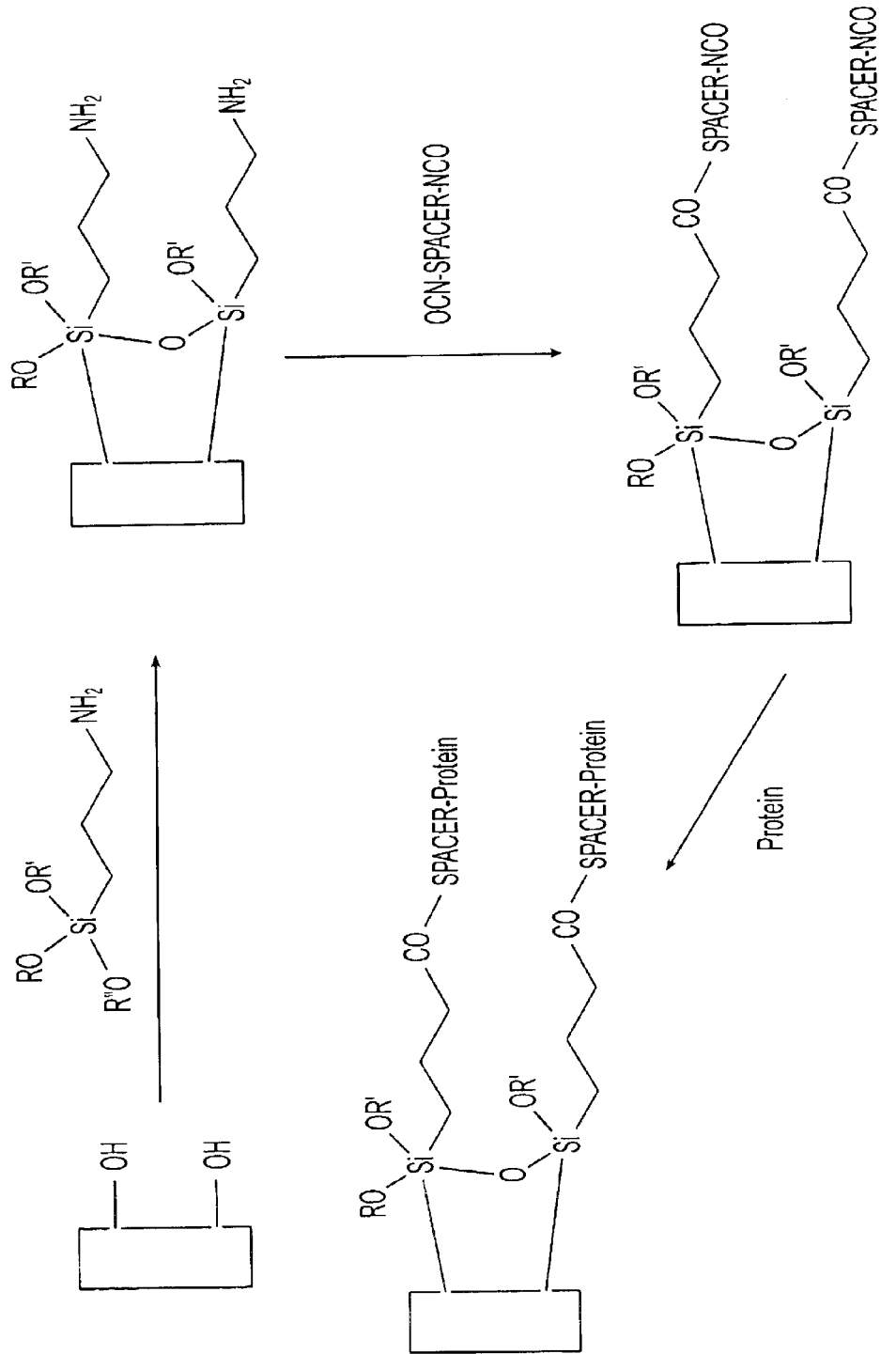

Various aspects of the invention are understood with reference to the following figures:

FIG. 1 represents a side view of a material of the invention, wherein regions of a functional additive are embedded within a porous plastic substrate;

FIG. 2 provides a representation of the attachment of spacers of varying lengths to a porous substrate, followed by the attachment of chemical or biological moieties to those spacers;

FIG. 3 represents a material of the invention which comprises a spacer covalently bound to a porous substrate, but bound to a chemical or biological moiety by a non-covalent bond;

FIG. 4 provides a synthetic scheme whereby a chemical or biological moiety can be covalently attached to a porous substrate of the invention via an amine-terminated silane spacer;

FIG. 5 provides a synthetic scheme whereby a chemical or biological moiety can be covalently attached to a porous substrate of the invention via an aldehyde-terminated silane spacer; and FIG. 6 provides a synthetic scheme which allows the lengthening of a spacer connecting a porous substrate and a chemical or biological moiety.

4. DETAILED DESCRIPTION OF THE INVENTION

Many plastics do not contain reactive functional groups (e.g. hydroxyl or amine groups) that can be used to attach chemical or biological moieties to surfaces of materials made from them. The surfaces of such materials can therefore be difficult to modify. This invention is based on a discovery that the surface properties of porous plastic materials can be altered in a controllable fashion by incorporating varying amounts of functional additives into those materials. Functional additives are materials that contain functional groups to which biological and/or chemical moieties can be covalently attached.

FIG. 1 depicts various aspects of materials of the invention. In particular, it provides a representation of a porous substrate made of a plastic and a functional additive. Portions of the functional additive that are exposed on the surface of the substrate provide functional groups (represented in FIG. 1 as "Fn") to which chemical or biological moieties (represented by "CBM") can be covalently bound. Alternatively, a spacer can connect a chemical or biological moiety to the surface. Preferably, the plastic that surrounds the regions of functional additives contains few, if any, functional groups. Alternatively, the plastic may contain functional groups that are less reactive under certain reaction conditions than the functional groups of the functional additive, such that chemical or biological moieties can be bound primarily to exclusively to regions of functional additive.

As discussed elsewhere herein, the polymer (e.g., plastic) from which the porous substrate is made is selected to provide a substrate of desired strength, flexibility, porosity, and resistance to degradation. Other factors, such as cost and biocompatibility may also play a role in its selection. The chemical or biological moiety(ies) bound to the substrate are selected to provide a final material with desired chemical and/or physical properties, while the type and amount of functional additive(s) are selected to affect the number and/or density of chemical or biological moieties bound to the substrate. For example, the chemical reactivity of functional groups provided by the functional additive can affect the number of moieties attached to the substrate surface.

Examples of chemical and/or physical properties conveyed by the covalent bonding of chemical or biological moieties to the surface of a porous substrate include, but are not limited to, increased hydrophilicity and biocompatibility. Indeed, the surfaces of preferred materials of the invention are hydrophilic, and can readily accept high surface tension fluids. Examples of high surface tension fluids include, but are not limited to, water, and aqueous salt and protein solutions. Hydrophilic substrates typically have a surface energy of greater than about 40 $dyn/cm^2$, more typically greater than about 60 $dyn/cm^2$.

Materials of the invention can be used in a variety of applications. For example, biocompatible materials can be used to provide temporary or permanent implants such as, but not limited to, soft or hard tissue prosthesis, artificial organs or organ components, or lenses for the eye such as contact or intraocular lenses. Biocompatible materials of the invention reduce or avoid undesirable reactions such as, but not limited to, blood clotting, tissue death, tumor formation, allergic reaction, foreign body rejection, and inflammation reaction. Preferred implants of the invention can be easily fabricated and sterilized, and will substantially maintain their physical properties and function during the time they remain implanted in, or in contact with, tissues and biological fluids.

Materials of the invention can also be used as, and within, medical devices. Examples of medical devices include, but are not limited to, dialysis tubing and membranes, blood oxygenator tubing and membranes, ultrafiltration membranes, diagnostic sensors (e.g., ELISA and sandwich assays), and drug delivery devices.

4.1. Porous Substrates

As shown in FIG. 1, typical materials of the invention comprise a porous substrate made of at least one plastic and at least one functional additive. The relative amounts and types of plastic(s) and functional additive(s) used to provide a substrate depend on the desired properties (e.g., strength, flexibility, and utility) of that material. For example, the strength and flexibility of a substrate will typically increase as the amount of functional additive it contains decreases. But the number of functional groups on the surface of a substrate will typically increase as the amount of functional additive it contains increases, although it is possible to concentration functional additive at a particular surface of a substrate.

Polymers (e.g., plastics) used to provide typical substrates have few—if any—functional groups to which chemical, biological, and other moieties (e.g., spacers) can be attached. Typical plastics are hydrophobic, and have a surface energy of less than about 40 $dyn/cm^2$, and more typically less than about 30 $dyn/cm^2$. Preferred plastics can be easily sintered or otherwise shaped to provide strong, durable, and/or flexible porous materials.

Examples of plastics that can be used to provide suitable substrates include, but are not limited to, polyolefins, polyethers, nylons, polycarbonates, poly(ether sulfones), or mixtures thereof. Preferred plastics are polyolefins. Examples of polyethers include, but are not limited to, polyether ether ketone (PEEK, poly(oxy-1,4-phenylene-oxy-1,4-phenylene-carbonyl-1,4-phenylene)), polyether sulfone (PES), or mixtures thereof. Examples of polyolefins include, but are not limited to, ethylene vinyl acetate;

ethylene methyl acrylate; polyethylenes; polypropylenes; ethylene-propylene rubbers; ethylene-propylene-diene rubbers; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); poly(tetrafluoroethylene) (PTFE); poly(vinylidene fluoride) (PVDF); acrylonitrile-butadiene-styrene (ABS); or mixtures thereof. Preferred polyolefins are polyethylene or polypropylene. Examples of suitable polyethylenes include, but are not limited to, low density polyethylene, linear low density polyethylene, high density polyethylene, ultra-high molecular weight polyethylene, or derivatives thereof.

Because typical plastics possess no functionality and are hydrophobic, porous substrates made from them according to this invention comprise at least one type of functional additive. Functional additives are materials that contain functional groups to which biological and/or chemical moieties can be covalently attached. Examples of functional groups include, but are not limited to, hydroxyl, carboxylic acid, anhydride, acyl halide, alkyl halide, aldehyde, alkene, amide, amine, guanidine, malimide, thiol, sulfonate, sulfonyl halide, sulfonyl ester, carbodiimide, ester, cyano, epoxide, proline, disulfide, imidazole, imide, imine, isocyanate, isothiocyanate, nitro, or azide. Preferred functional groups are hydroxyl, amine, aldehyde, or carboxylic acid. A particularly preferred functional group is hydroxyl.

Mixtures of functional groups can be provided in controlled ratios by including two or more additives within a substrate, or by using an additive that contains more than one type of functional group. The presence, types, and densities of functional groups on the surface of a substrate can be readily determined by methods such astitration, fourier transform infrared spectroscopy (FTIR), attenuated total reflectance (ATR), and X-ray photoelectron spectroscopy (XPS), or using molecular probes such as, D-1557 sulfonyl chloride, fluorescein isothiocyanate, fluorescein dichlorotriazine, and the like.

Preferred functional additives are inexpensive, and can be readily incorporated into porous substrates without degrading (e.g., losing their functionality) during the thermal process. Examples of functional additives include, but are not limited to, silica powder, silica gel, chopped glass fiber, glass beads, ground glass fiber, or glass bubbles. Preferred functional additives are silica powder or glass fiber, which provide hydroxyl functional groups.

Substrates used to provide materials of the invention are porous, and consequently contain one or more channels through which gas or liquid molecules can pass. Preferred substrates have an average pore size of from about 10 $\mu$m to about 200 $\mu$m, more preferably from about 15 $\mu$m to about 50 $\mu$m, and most preferably from about 20 $\mu$m to about 30 $\mu$m. Mean pore size and pore density can be determined using, for example, a mercury porosimeter, or scanning electron microscopy.

Because porous substrates of the invention are made of a porous polymeric matrix into which inclusions of functional additive are trapped, a surface of a typical substrate will contain regions of functional additive surrounded by regions of the polymeric matrix. The surface density and size of the regions of functional additive will depend on a variety of factors, including the desired density of chemical or biological moieties to be attached to it. In a typical substrate of the invention, functional additive covers about 5% to about 60%, and more typically of about 10% to about 50% percent of the surface area of the substrate.

4.1.1. Preparation of Porous Substrates

A variety of methods known to those skilled in the art can be used to make porous substrates. Some examples include sintering; the use of blowing agents and/or leaching agents; microcell formation methods such as those disclosed by U.S. Pat. Nos. 4,473,665 and 5,160,674, both of which are incorporated herein by reference; drilling, including laser drilling; and reverse phase precipitation. Depending on how it is made, a porous substrate can thus contain regular arrangements of channels of random or well-defined diameters and/or randomly situated pores of varying shapes and sizes. Pore sizes are typically referred to in terms of their average diameters, even though the pores themselves are not necessarily spherical.

The particular method used to form the pores or channels of a porous substrate and the resulting porosity (i.e., average pore size and pore density) of the porous substrate can vary according to the desired application to which the final porous material will be put. The desired porosity of the substrate can also be affected by the substrate material itself, as porosity can affect in different ways the physical properties (e.g., tensile strength and durability) of different materials.

Preferred substrates of the invention are made by sintering a mixture comprising particles of at least one polymer (e.g., plastic) and particles of a functional additive (e.g., silica powder or chopped glass fiber). Optional additional materials such as, but not limited to, lubricants, colorants, and fillers can also be added to the mixture. The relative amounts of polymer and functional additive depend on the desired number and density of functional groups on the substrate surface and on the desired strength of the final material. As discussed elsewhere herein, the strength of a substrate may decrease as its functional additive content increases, although if the functional additive can adhere to the plastic surrounding it, this may not be the case.

The relative amounts of plastic and functional additive used to provide a porous substrate will vary with the specific materials used, the desired functionality of the substrate surface, and the strength and flexibility of the substrate itself. Typically, however, the mixture from which the porous substrate is made comprises from about 5% to about 60%, more preferably from about 10% to about 40%, and most preferably from about 20% to about 30% weight percent functional additive.

The polymer, functional additive, and optional additional materials are blended to provide a uniform mixture, which is then sintered. Depending on the desired size and shape of the final product (e.g., a block, tube, cone, cylinder, sheet, or membrane), this can be accomplished using a mold, a belt line such as that disclosed by U.S. Pat. No. 3,405,206, which is incorporated herein by reference, or other techniques known to those skilled in the art. In a preferred embodiment, the mixture is sintered in a mold. Suitable molds are commercially available and are well known to those skilled in the art. Specific examples of molds include, but are not limited to, flat sheets with thickness ranging from about ⅛ inch to about 0.5 inch and round cylinders of varying heights and diameters. Suitable mold materials include, but are not limited to, metals and alloys such as aluminum and stainless steel, high temperature thermoplastics, and other materials both known in the art and disclosed herein.

In a preferred embodiment, a compression mold is used to provide the sintered material. In this embodiment, the mold is heated to the sintering temperature of the plastic, allowed to equilibrate, and then subjected to pressure. This pressure typically ranges from about 1 psi to about 10 psi, depending on the composition of the mixture being sintered and the desired porosity of the final product. In general, the greater the pressure applied to the mold, the smaller the average pore size and the greater the mechanical strength of the final product. The duration of time during which the pressure is applied also varies depending on the desired porosity of the final product, and is typically from about 2 to about 10 minutes, more typically from about 4 to about 6 minutes. In another embodiment of the invention, the mixture is sintered in a mold without the application of pressure.

Once the porous substrate has been formed, the mold is allowed to cool. If pressure has been applied to the mold, the cooling can occur while it is still being applied or after it has been removed. The substrate is then removed from the mold and optionally processed. Examples of optional processing include, but are not limited to, sterilizing, cutting, milling, polishing, encapsulating, and coating.

Using methods such as that described above, a variety of materials of varying sizes and shapes can be used to provide a suitable porous substrate. In one embodiment, similarly-sized particles of plastic and/or functional additive are sintered. In this embodiment, the particles' size distribution is preferably narrow (e.g., as determined using commercially available screens). This is because it has been found that particles of about the same size can be consistently packed into molds, and because a narrow particle size distribution allows the production of a substrate with uniform porosity (i.e., a substrate comprising pores that are evenly distributed throughout it and/or are of about the same size). This is advantageous because solutions and gases tend to flow more evenly through uniformly porous materials than those which contain regions of high and low permeability. Uniformly porous substrates are also less likely to have structural weak spots than substrates which comprise unevenly distributed pores of substantially different sizes. In view of these benefits, if a polymer is commercially available in powder (i.e., particulate) form, it is preferably screened prior to use to ensure a desired average size and size distribution. However, many polymers are not commercially available in powder form. Consequently, methods such as cryogenic grinding and underwater pelletizing can be used to prepare powders of them.

Cryogenic grinding is a well-known method, which can be used to prepare particles of plastic and functional additive of varying sizes. But because cryogenic grinding provides little control over the sizes of the particles it produces, powders made by it may have to be screened to ensure that the particles to be sintered are of a desired average size and size distribution.

Plastic particles can also be made by underwater pelletizing. Underwater pelletizing is described, for example, in U.S. patent application Ser. No. 09/064,786, filed Apr. 23, 1998, and U.S. Provisional Patent Application No. 60/044, 238, filed Apr. 24, 1999, both of which are incorporated herein by reference. Although this method is typically limited to the production of particles with diameters of at least about 36 $\mu$M, it offers several advantages. First, underwater pelletizing provides accurate control over the average size of the particles produced, in many cases thereby eliminating the need for an additional screening step and reducing the amount of wasted material. A second advantage of underwater pelletizing is that it allows significant control over the particles' shape.

Thermoplastic particle formation using underwater pelletizing typically requires an extruder or melt pump, an underwater pelletizer, and a drier. The thermoplastic resin is fed into an extruder or a melt pump and heated until semi-molten. The semi-molten material is then forced through a die. As the material emerges from the die, at least one rotating blade cuts it into pieces herein referred to as "pre-particles." The rate of extrusion and the speed of the rotating blade(s) determine the shape of the particles formed from the pre-particles, while the diameter of the die holes determine their average size. Water, or some other liquid or gas capable of increasing the rate at which the pre-particles cool, flows over the cutting blade(s) and through the cutting chamber. This coagulates the cut material (i.e., the pre-particles) into particles, which are then separated from the coolant (e.g., water), dried, and expelled into a holding container.

The average size of particles produced by underwater pelletizing can be accurately controlled and can range from about 0.014" (35.6 $\mu$M) to about 0.125" (318 $\mu$M) in diameter, depending upon the porous substrate. Average particle size can be adjusted simply by changing dies, with larger pore dies yielding proportionally larger particles. The average shape of the particles can be optimized by manipulating the extrusion rate and the temperature of the water used in the process.

While the characteristics of a porous material can depend on the average size and size distribution of the particles used to make it, they can also be affected by the particles' average shape. Consequently, in another embodiment of the invention, the particles of plastic and functional additive particles are substantially spherical. This shape facilitates the efficient packing of the particles within a mold. Substantially spherical particles, and in particular those with smooth edges, also tend to sinter evenly over a well defined temperature range to provide a final product with desirable mechanical properties and porosity.

In a specific embodiment of the invention, the particles of plastic and/or functional additive are substantially spherical and free of rough edges. Consequently, if the particles used in this preferred method are commercially available or made by cryogenic grinding, they are thermal fined to ensure smooth edges, and are screened to ensure a proper average size and size distribution. Thermal fining is a well-known process wherein particles are rapidly mixed and optionally heated such that their rough edges become smooth. Mixers suitable for thermal fining include the W series high-intensity mixers available from Littleford Day, Inc., Florence, Ky.

Particles made by underwater pelletizing, which allows precise control over particle size and can yield smooth, substantially spherical particles, typically do not need to be thermal fined or screened.

4.2. Substrate Surface Modification

Once the porous substrate has been formed, chemical and/or biological moieties are bound directly or indirectly to its surface. FIG. 2 provides a representation of this process wherein a spacer molecule (e.g., an alkane substituted with at least one functional group) is attached to the surface of a substrate to provide an intermediate material. Chemical or biological moieties such as proteins are then attached to the spacer. Also as shown in FIG. 2, the length of the spacer can be optionally increased by reacting the intermediate material with additional chemical moieties to provide a second intermediate material, to which chemical or biological moieties can be attached.

As used herein, spacers are differentiated from chemical or biological moieties only by their use in a particular instance. To be specific, a chemical or biological moiety is something that provides, at least to a substantial degree, the useful physical or chemical properties of a particular material. For example, the chemical or biological moiety in a material to be used as a biosensor will be a moiety that can recognize, bond, or associate with the molecule(s) to be detected. By contrast, a spacer is a chemical moiety that provides some distance between the surface of the porous substrate and the chemical or biological moiety. Still, a spacer can augment or facilitate the activity or utility of a chemical or biological moiety by removing it from the surface of the substrate. It will be readily apparent to those of skill in the art, however, that a moiety used as a spacer in one instance can be the chemical or biological moiety in another.

Spacers and biological or chemical moieties that are directly bound to the substrate surface are bound covalently or though strong multi-point non-covalent interactions. However, bonds between moieties bound to the surface and other moieties not bound to the surface need not be covalent. For example, FIG. 3 represents a material comprised of a spacer covalently attached to a porous substrate, wherein the spacer can form ligand-receptor or hybridization-type bonding with a pharmacologically active chemical or biological moiety. In a specific example of a material encompassed by the representation of FIG. 3, the spacer is an oligonucleotide, and the chemical or biological moiety comprises an oligonucleotide or polynucleotide complementary to the spacer.

The invention further encompasses spacers that are capable of selectively releasing an immobilized chemical or biological moiety. For example, a drug may be attached to a spacer by a bond that readily hydrolyzes under physiological conditions, or which breaks when exposed to radiation of a particular energy. Such materials can be useful for the controlled release of drugs.

In order to form a covalent bond between the substrate surface and a moiety, a functional group on the surface must be complementary to a functional group on the chemical precursor of the moiety. In other words, functional groups on the surface and on the precursor to whatever will be attached to it must be capable of forming a covalent bond under suitable reaction conditions. An example of complementary groups is amine and aldehyde, which can react to form a bond under suitable conditions. Other complementary pairs of functional groups will be readily apparent to those skilled in the art.

Examples of spacers include, but are not limited to, silanes, silane aldehydes, diamines, alcohols, esters, glycols (such as polyethylene glycol), anhydrides, dialdehydes, terminal difunctionalized polyurethanes, succinic acid, diaminohexanes, glyoxylic acids, glycines, dentrimers, multifunctional polymers, and diones. Preferred spacers are those of Formula I:

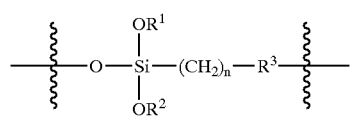

Formula I wherein the bond broken by a wavy line are those between the spacer and the substrate or other moieties; $R^1$ and $R^2$ each independently is hydrogen, substituted or unsubstituted alkyl, aryl, or aralkyl; $R^3$ is a substituted or unsubstituted aliphatic chain or a bond; and n is an integer from about 1 to about 18, preferably n is an integer from about 1 to about 10, and more preferably n is about 2 to about 5. More preferred spacers are those of Formula VIII:

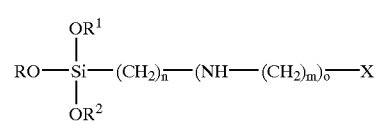

Formula VIII wherein $R^1$, $R^2$, and n are as defined above; R is the surface of the porous substrate; X is a group capable of bonding to a biological or chemical moiety, such as OH, $NH_2$, CHO, $CO_2H$, NCO, epoxy, and the like; m is an integer from about 1 to about 5; o is an integer from 0 to about 3; most preferably, X is $NH_2$ or CHO.

Other more preferred spacers are those of Formula IX:

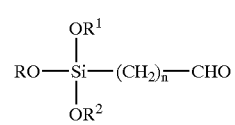

Formula IX wherein R, $R^1$, $R^2$, and n are as defined above.

A wide array of chemical and biological moieties can be attached directly or via a spacer to the surface of a porous substrate. Examples of such moieties include, but are not limited to, drugs (e.g., pharmaceuticals), hydrophilic moieties, catalysts, antibiotics, antibodies, antimycotics, carbohydrates, cytokines, enzymes, glycoproteins, lipids, nucleic acids, nucleotides, oligonucleotides, peptides, polynucleotides, proteins, cells, ligands, ribozymes, or combinations thereof.

4.2.1. Functionalization of Substrates

A porous substrate is functionalized according to the invention by the covalent bonding of a molecule (e.g., a spacer or chemical or biological moiety) to its surface. The molecule can often be directly attached to the surface of the substrate. However, it is sometimes desirable to attach a chemical or biological moiety to a substrate indirectly by means of a spacer.

For example, if a biological moiety is to interact with molecules in solution, it may interact with such molecules more readily if positioned at some distance from the surface to which it is attached. Alternatively, the shape and size of some biological moieties can prevent the formation of covalent bonds between them and functional groups on a substrate surface. In such cases, a spacer is used to link the moiety to the surface.

FIG. 4 illustrates a method by which amine-functionalized chemical or biological moieties can be attached to the surface of a substrate of the invention. In this method, a silane with a terminal amine reacts with a hydroxyl group provided by a functional additive such as silica powder embedded in the surface. The terminal amine of the resulting material can then be converted to an aldehyde using, for example, an excess of glutaraldehyde. The resulting product is then contacted with an amine-functionalized chemical or biological moiety (e.g., a protein) the under suitable conditions to form a material of the invention. FIG. 5 shows a related method, wherein the silane initially reacted with the substrate surface already has a terminal aldehyde, which can react with amine-functionalized chemical or biological moieties.

In some cases, a spacer such as that shown in FIG. 4 and FIG. 5 is of insufficient length to provide a useful material, i.e., a desirable environment for the bioactive substance. In such cases, the length of the spacer can be increased using methods readily apparent to those skilled in the art. One example is shown in FIG. 6. According to this method, a silane with a terminal amine reacts with a hydroxyl group provided by a functional additive such as silica powder embedded in the surface. The resulting material is then contacted under suitable conditions with a compound of Formula VI:

Z-Spacer-Z  Formula VI wherein Spacer is a hydrophilic segment and Z is a terminal group capable of covalently or non-covalently bonding to proteins, amino acids, oligonucleotides, and the like. Preferably, Spacer is hydrophilic polyurethane, polyethylene glycol, or polyelectrolytes with terminal groups (Z) capable of bonding to proteins, amino acids, oligonucleotides wherein Z includes, but is not limited to, isocyanurate, aldehydes, amino, carboxylic acids, N-hydroxysuccimide, and the like. In a more preferred compound of Formula VI, Spacer is hydrophilic polyurethane (NCO-hydrophilic polyurethane-NCO) or N-hydroxysuccimide-PEG-N-hydroxysuccimide (PEG-NHS). The resulting complex is then contacted with an amine-functionalized chemical or biological moiety under reaction conditions suitable for the formation of a covalent bond.

5. EXAMPLES

Certain embodiments of the invention, as well as certain novel and unexpected advantages of the invention, are illustrated by the following non-limiting examples. Materials were purchased from Sigma-Aldrich Co. (Milwaukee, Wis.).

5.1 Example 1

Preparation of a Hydrophilic Polyurethane Spacer

A reaction flask was charged under nitrogen with 4,4'-methylenebis(cyclohexyl isocyanate) (5.8 g), dibutyltin bis (ethyl hexanoate) (30 mg), and THF (10 g). Using a heating mantle, the reaction flask was gently warmed to 65° C. Subsequently, a solution of polyethylene glycol (PEG 1000) (MW=1000, 11.2 g) dissolved in 25 g of THF was added dropwise to the reaction flask. After the addition was complete, the reaction was allowed to proceed for 12 hours at 65° C. under nitrogen. The resulting solution, a light-yellow and transparent gel, was poured out of the reaction flask and stored in a sealed glass bottle filled with dry nitrogen.

5.2 Example 2

Preparation of a Porous Plastic with Glass Powder as Dopant

Glass bubble (amorphous silica, CAS No. 7631-86-9) supplied by 3M (St. Paul, Minn.) was blended with an ultra high molecular weight polyethylene powder GUR 2122 by TICONA (Summit, N.J.) at 20% by weight. After the mixture was well blended, it was placed into a 0.25 inch flat mold. Using an electrically heated plate, the mold was heated to and was kept at 140° C. for 4 minutes. A skilled artisan can readily determine the amount of time to heat the mold, depending upon the thickness of the final product. After heating, the mold was cooled and the porous plastic with immobilized glass bubbled was removed.

5.3 Example 3

Preparation of a Functionalized Porous Material (Method 1)

Binding buffer (10 mM phosphate; pH 7.5, 0.015 M NaCl). 0.192 g $NaH_2PO_4$, 2.252 g $Na_2HPO_4 \cdot 7H_2O$ and 0.27 g of NaCl are dissolved in 800 ml deionized (DI) water. The pH 7.5 is adjusted with 1N HCl/1N NaOH, and the volume is brought to 1000 ml with DI water. The buffer is then purged with nitrogen before coupling procedure.

Washing buffer: (10 mM phosphate, pH 7.5, 1.0 M NaCl). 5.844 g NaCl is dissolved in 100 ml of binding buffer.

Storage buffer: (10 mM phosphate, pH 7.5, 0.15M NaCl, 0.02% $NaN_3$).

Silica powder incorporated substrate, prepared in Example 2, is washed with alcohol, filtered, and air dried. After the substrate has been completely dried, they are immersed into a silane solution (5% of 3-aminopropyltriethoxysilane/isopropanol solution, CAS #: 919-30-2) until the substrate is completely wet. The substrate is removed from the solution and air dried. After the substrate is half-dried, it is placed into an oven at about 60 to 70° C. for about 30 minutes. After the substrate is completely dried, it is submerged in a glutaraldehyde/alcohol solution (20%) for about 20 minutes. The substrate is dried again in the oven for 30 minutes. Finally, the reactive substrate is dipped into protein/binding buffer solution (0.1 mg/ml IgG solution) and mixed gently for 24 hours at 4° C. The binding buffer of unreacted protein solution is drained from the matrix. The functionalized porous material is then immersed in a washing buffer (pH 7.5), and sodium cyanoborohydride is added until the final concentration is approximately 1.0 M. The functionalized porous material is washed with washing buffer (pH 7.5) until all excess sodium cyanoborohydride is removed and immersed in storage buffer at 4° C.

5.4 Example 4

Preparation of a Functionalized Porous Material (Method 2)

The silica powder incorporated substrate, prepared in Example 2) is washed and dried as described above. The substrate is immersed into a silane solution (5% of aldehyde trimethoxysilane/isopropanol solution) until the substrate is completely wet. Aldehyde methoxysilane was supplied by United Chemical Corporation, Piru, Calif. The substrate is filtered out of the solution and rinsed with anhydrous isopropanol. The substrate is then air dried. After the substrate is half-dried, the substrate is placed in an oven at about 60° C. to 70° C. for 30 minutes. The reactive substrate is dipped into protein/binding buffer solution (0.1 mg/ml IgG solution) and mixed gently for 24 hours at 4° C. The binding buffer of unreacted protein solution is drained, and the substrate is immersed in washing buffer (pH 7.5). Sodium cyanoborohydride is added until the final concentration is approximately 1.0 M. The functionalized porous material is then washed with washing buffer (pH 7.5) until all excess sodium cyanoborohydride is removed and immersed in storage buffer at 4° C.

5.5 Example 5

Preparation of a Functionalized Porous Material (Method 3)

In a separate procedure, the silica powder incorporated substrate is washed with alcohol, filtered, and air dried. After the substrate has been completely dried, it is immersed into a silane solution (5% of 3-aminopropyltriethoxysilane/isopropanol solution, CAS #: 919-30-2) until completely wet. The substrate is filtered out of the solution and air dried. The substrate is half-dried and placed in an oven at about 60 to 70° C. for 30 minutes. After the substrate is completely dried it is submerged into hydrophilic polyurethane/tetrahydrofuran (THF) solution for about 6 hours. The preparation of the hydrophilic polyurethane was described in Example 5.1. The synthesis of other suitable hydrophilic polyurethanes was described in U.S. patent application Ser. No. 09/375,383, which is incorporated herein by reference. The substrate is then filtered out of the solution and rinsed with dry THF. The washed substrate is then dried in a vacuum oven to drive off the residual THF. Finally, the reactive substrate is dipped into a protein/binding buffer solution (0.1 mg/ml IgG solution) and mixed gently for 24 hours at 4° C. The binding buffer of unreacted protein solution is drained, and the substrate is immersed in washing buffer (pH 7.5). Sodium cyanoborohydride is added until the final concentration is approximately 1.0. The functionalized porous material is washed with washing buffer (pH 7.5) until all excess sodium cyanoborohydride is removed and immersed in storage buffer at 4° C.

5.6. Example 6

Detection of Functional Groups

The hydroxyl functionality of the substrate can be characterized in several ways. For example, X-ray photoelectron spectroscopy (XPS) can offer the elemental information about oxygen. Also, Fourier Transform Infra-red Sprectroscopy (FTIR) can reveal certain chemical structures, such as hydroxyl. Direct measurement of surface R—OH concentrations can be carried out by using the molecular probe D-1557 sulfonyl chloride from Molecular Probes Inc., of Eugene, Oreg. after reaction of the base hydrolysis (which releases the chromophore) of the sulfonic acid ester formed by reaction of the D-1557 probe (1 mg/ml in cry acetone with 1.0% pyridine) of the hydroxyl functionalized polymer surface.

Detection of amine groups can be carried out in several ways. Amine selective molecular probes such as fluorescein isothiocyanate (FITC) and fluorescein dichlorotriazine (DTAF) react with all functionalized surfaces throughout the porous polyethylene article, while being unreactive with the unmodified surfaces. Cleavage of the isothiourea formed by reaction of FITC with alkyl amine functions with aqueous 0.1 M NaOH releases fluorescein into solution for direct spectrophotometric measurement and the number of micromoles of amine function per gram of porous solid can be calculated. The amino groups on an aminated specimen can also be determined chemically according to R. Allul (*DNA Probes*, H. G. Keller et al. eds., Macmillan, New York (1993)). Thus, the aminated specimen is treated with 3-O-4-(nitrophenylsuccinylated)-5'-O-DMT-deoxyribonucleoside, followed by blockage of unreached amines with pyridine/acetic anhydride/N-methyl imidazole (8:1:1, v:v:v). The amount of bound deoxyribonucleoside is determined by absorbance at 498 nm after treatment with 70% aqueous perchloric acid, toluenesulfonic acid in acetonitrile, commercial deblock preparations, or the like, to release the DMT group from the support.

Another method for the detection of amino functional groups is carried out as follows. Amino functional porous plastics (1 g) cut into 1 mm particles are mixed with a 0.2 mM Sulfo-SDTB solution, made by dissolving 3 mg of Sulfo-SDTB into 25 ml 0.025 M $NaHCO_3$ buffer solution (pH 8.5) at room temperature for one hour. Remove the porous plastics and rinse three times with 15 ml of deionized water for 10 min. Add the rinsed porous plastics to 10 ml of 50% perchloric acid water solution and shake at room temperature for 15 min. Remove a 3 ml sample and measure the absorbency at a 498 nm wavelength with a 1 cm path length UV cuvette. The amino functional group density can be calculated by C(M amino group/gram porous plastic)= 3.3(As−Af)/70000.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the invention are to be included as further embodiments of the invention. The scope of the invention accordingly is to be defined as set forth in the appended claims.

What is claimed is:

1. A material comprising:
   - a porous substrate comprising a sintered mixture of polymer particles and functional additive particles, wherein the porous substrate has a surface that comprises at least one of the functional additive particles;
   - a spacer covalently bound to the at least one functional additive particle; and
   - a biological or chemical moiety covalently or non-covalently bound to the spacer.

2. The material of claim 1, wherein the polymer particles are made of a polymer which is a polyolefin, polyether, nylon, polycarbonate, poly(ether sulfone), or a mixture thereof.

3. The material of claim 2, wherein the polyolefin is ethylene vinyl acetate; ethylene methyl acrylate; polyethylenes; polypropylenes; ethylene-propylene rubbers; ethylene-propylene-diene rubbers; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); poly(tetrafluoroethylene) (PTFE); poly(vinylidene fluoride) (PVDF); acrylonitrile-butadiene-styrene (ABS); or a mixture thereof.

4. The material of claims 2, wherein the polyolefin is polyethylene or polypropylene.

5. The material of claim 2, wherein the polyether is polyether ether ketone (PEEK), (poly(oxy-1,4-phenylene-oxy-1,4-phenylene-carbonyl-1,4-phenylene)), polyether sulfone (PES), or a mixture thereof.

6. The material of claim 1, wherein the functional additive comprises a hydroxyl, carboxylic acid, anhydride, acyl halide, alkyl halide, aldehyde, alkene, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide functional group.

7. The material of claim 6, wherein the functional additive comprises a hydroxyl, amine, aldehyde, or carboxylic acid functional group.

8. The material of claim 7, wherein the functional additive comprises a hydroxyl functional group.

9. The material of claim 1, wherein the functional additive is silica powder, silica gel, chopped glass fiber, controlled porous glass (CPG), glass beads, ground glass fiber, glass bubbles, kaolin, alumina oxide, or a mixture thereof.

10. The material of claim 1, wherein the spacer is a silane, functionalized silane, diamine, alcohol, ester, glycol, anhydride, dialdehyde, terminal difunctionalized polyurethane, dione, macromer, or a multifunctional polymer.

11. The material of claim 10, wherein the spacer is of Formula I:

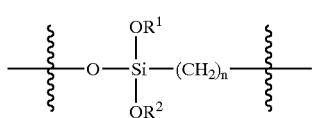

Formula I wherein $R^1$ and $R^2$ are each independently hydrogen, substituted or unsubstituted alkyl, aryl, or aralkyl; and n is an integer from about 1 to about 18.

12. The material of claim 1, wherein the chemical or biological moiety is a drug, hydrophilic moiety, catalyst, antibiotic, antibody, antimycotic, carbohydrate, cytokine, enzyme, glycoprotein, lipid, nucleic acid, nucleotide, oligonucleotide, peptide, protein, ligand, cell, ribozyme, or a combination thereof.

13. The material of claim 10 wherein the spacer to which the porous substrate and biological or chemical moiety is attached is of Formula VIII:

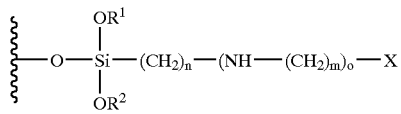

Formula VIII wherein the porous substrate is bound to the oxygen atom; $R^1$ and $R^2$ each independently is hydrogen, substituted or unsubstituted alkyl, aryl, or aralkyl; X is OH, $NH_2$, CHO, $CO_2H$, NCO, or epoxy; n is an integer from about 1 to about 5; m is an integer from about 1 to about 5; and o is an integer from 0 to about 3.

14. The material of claim 13 wherein X is CHO or $NH_2$.

15. The material of claim 10 wherein the spacer to which the porous substrate and biological or chemical moiety is attached is of Formula IX:

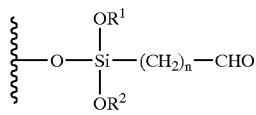

Formula IX wherein the porous substrate is bound to the oxygen atom; $R^1$ and $R^2$ each independently is hydrogen, substituted or unsubstituted alkyl, aryl, or aralkyl; and n is from about 1 to about 18.

16. A material comprising:
a porous substrate comprising sintered polyethylene particles and having a surface in which at least one particle of a functional additive has been embedded; and
a spacer precursor of Formula II covalently attached to the at least one particle of functional additive:

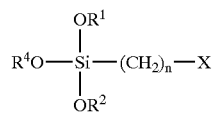

Formula II wherein $R^1$, $R^2$ and $R^4$ are each independently hydrogen, substituted or unsubstituted alkyl, aryl, or aralkyl; n is an integer from about 1 to about 18; and X is OH, $NH_2$, CHO, $CO_2H$, NCO, or epoxy.

17. A material comprising:
a porous substrate comprising sintered polyethylene particles and having a surface in which at least one particle of a functional additive has been embedded; and
a spacer of Formula I:

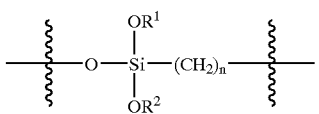

Formula I wherein $R^1$ and $R^2$ are each independently hydrogen, substituted or unsubstituted alkyl, aryl, or aralkyl; and n is an integer from about 1 to about 18; and wherein the spacer is covalently attached to the at least one particle of functional additive and to a chemical or biological moiety.

18. The material of claim 17, wherein the chemical or biological moiety is a nucleotide, oligonucleotide, polynucleotide, peptide, cell, ligand, or protein.

19. A method of providing a material which comprises:
sintering particles of a polymer and particles of a functional additive having functional groups to provide a porous substrate having a surface, wherein the surface comprises at least one of the functional groups;
attaching a spacer to at least one particle of functional additive by contacting a functional group of the at least one particle of functional additive with the spacer under reaction conditions suitable for the formation of a covalent bond between an atom of the functional group and an atom of the spacer; and
contacting the spacer with a chemical or biological moiety under reaction conditions suitable for the formation of a covalent or non-covalent bond between an atom of the spacer and an atom of the chemical or biological moiety.

20. The method of claim 19, wherein the functional group is hydroxyl, carboxylic acid, anhydride, acyl halide, alkyl halide, aldehyde, alkene, amide, amine, guanidine, malimide, thiol, sulfonate, sulfonic acid, sulfonyl ester, carbodiimide, ester, cyano, epoxide, proline, disulfide, imidazole, imide, imine, isocyanate, isothiocyanate, nitro, or azide.

21. The method of claim 19, wherein the porous substrate is formed by sintering the particles of functional additive and then attaching the spacer, or attaching the spacer to at least one of the particles of functional additive prior to sintering the particles.

22. A method of providing a material which comprises:
sintering particles of a polymer and particles of a functional additive having functional groups to provide a porous substrate having a surface, wherein the surface comprises at least one of the functional groups; and
contacting the at least one at the functional groups with a compound of Formula II:

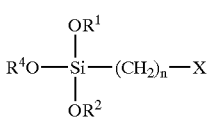

Formula II wherein each of $R^1$, $R^2$, and $R^4$ each independently is hydrogen, substituted or unsubstituted alkyl, aryl, or aralkyl; n is an integer from about 1 to about 18; and X is OH, $NH_2$, CHO, $CO_2H$, NCO, or epoxy under conditions suitable for the formation of a material of Formula III:

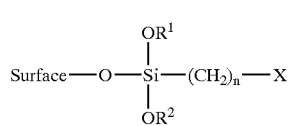

Formula III wherein Surface is the surface of the porous substrate.

23. The method of claim 22 wherein the material of Formula III is contacted with a chemical or biological moiety having an amine group if X is an aldehyde or carboxylic acid, or a chemical or biological moiety having an aldehyde or carboxylic acid group if X is an amine, under reaction conditions suitable for the formation of a material of Formula IV:

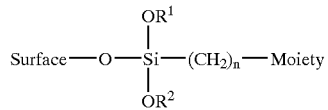

Formula IV wherein Moiety is the chemical or biological moiety, and wherein Surface is the surface of the porous substrate.

24. The method of claim 22 wherein X is $NH_2$ in the material of Formula III, and the material is contacted with a compound of Formula V:

Formula V wherein Spacer is a hydrophilic segment and Z is a terminal group capable of covalently or non-covalently bonding to proteins, amino acids, oligonucleotides, under reaction conditions suitable for the formation of a material of Formula VI:

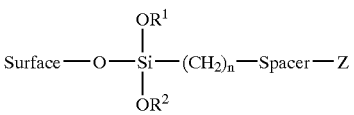

Formula VI wherein Surface is the surface of the porous substrate.

25. The method of claim 24, wherein Spacer is a hydrophilic polyurethane, polyethylene glycol, or polyelectrolyte and wherein Z is isocyanurate, aldehyde, amino, carboxylic acid, or N-hydroxysuccimide.

* * * * *